(12) United States Patent
Liu et al.

(10) Patent No.: US 11,906,481 B1
(45) Date of Patent: Feb. 20, 2024

(54) GROUTING AND WATER-PLUGGING DEVICE FOR FRACTURED ROCK IN MINE COUPLING STATE, AND TEST METHOD

(71) Applicant: SHANDONG UNIVERSITY OF SCIENCE AND TECHNOLOGY, Qingdao (CN)

(72) Inventors: Weitao Liu, Qingdao (CN); Haifeng Wu, Qingdao (CN); Xiangxi Meng, Qingdao (CN); Yanhui Du, Qingdao (CN); Lifu Pang, Qingdao (CN); Mengke Han, Qingdao (CN); Jiyuan Zhao, Qingdao (CN)

(73) Assignee: SHANDONG UNIVERSITY OF SCIENCE AND TECHNOLOGY, Shandong (CN)

( * ) Notice: Subject to any disclaimer, the term of this patent is extended or adjusted under 35 U.S.C. 154(b) by 0 days.

(21) Appl. No.: 18/554,576

(22) PCT Filed: Jun. 8, 2022

(86) PCT No.: PCT/CN2022/097501
§ 371 (c)(1),
(2) Date: Oct. 9, 2023

(87) PCT Pub. No.: WO2023/165043
PCT Pub. Date: Sep. 7, 2023

(30) Foreign Application Priority Data

Mar. 4, 2022 (CN) .......................... 202210206727.X

(51) Int. Cl.
*G01N 3/12* (2006.01)
*G01N 33/24* (2006.01)
(52) U.S. Cl.
CPC ............... *G01N 3/12* (2013.01); *G01N 33/24* (2013.01)

(58) Field of Classification Search
CPC .................................. G01N 3/12; G01N 33/24
(Continued)

(56) References Cited

FOREIGN PATENT DOCUMENTS

| CN | 101813604 A | * | 8/2010 |
| CN | 101813604 A | | 8/2010 |

(Continued)

OTHER PUBLICATIONS

Translation of CN-102419303-A (Year: 2012).*
(Continued)

*Primary Examiner* — Nathaniel T Woodward

(57) ABSTRACT

The present disclosure provides a grouting and water-plugging device for a fractured rock in a mine coupling state and a test method, and relates to the technical field of rock mechanics testing. The device includes a pressurizer, a reservoir, a test box, and a grouting pump. The reservoir includes a temperature sensor and a pressing-water plate. The pressing-water plate is connected to the pressurizer through a pressurizing rod. A pressure measuring pipe and a drainage pipe are installed on an outer side of the reservoir. The reservoir is connected to a water pump through a water injection pipe. The test box includes a rock, a transverse force exerting plate, a longitudinal force exerting plate, a stress sensor and the temperature sensor. The longitudinal force exerting plate is provided with multiple water through holes. A sliding box door is hinged to a front wall of the test box. The pressure measuring pipe and the drainage pipe are installed on a rear wall of the test box. The rear wall of the test box is connected to the grouting pump through a grouting pipe. A water pressure gauge is installed on the grouting pipe. Valves are installed on the grouting pipe, the pressure measuring pipe, the water injection pipe, and the drainage pipe. The device can be used to conduct a test, simulating coupling conditions of stress-temperature-water (Continued)

pressure in a mine, for a rock, and to verify the effectiveness of water plugging.

1 Claim, 1 Drawing Sheet

(58) Field of Classification Search
USPC .......................................................... 73/49.8
See application file for complete search history.

(56) References Cited

FOREIGN PATENT DOCUMENTS

| | | | |
|---|---|---|---|
| CN | 102419303 A | * | 4/2012 |
| CN | 102419303 A | | 4/2012 |
| CN | 203502388 U | | 3/2014 |
| CN | 104819898 A | | 8/2015 |
| CN | 104977234 A | | 10/2015 |
| CN | 105842424 A | | 8/2016 |
| CN | 107063962 A | | 8/2017 |
| CN | 212275532 U | | 1/2021 |
| JP | H0450636 A | | 2/1992 |
| JP | 2003294601 A | | 10/2003 |

OTHER PUBLICATIONS

Translation of CN-101813604-A (Year: 2010).*
"English translation of International Search Report of the China National Intellectual Property Administration", PCT International Application No. PCT/CN2022/097501 completed Nov. 10, 2022, dated Nov. 28, 2022, Beijing China (3 pages).
"English translation of Written Opinion of the China National Intellectual Property Administration", PCT International Application No. PCT/CN2022/097501 completed Nov. 21, 2022, dated Nov. 28, 2022, Beijing China (5 pages).
"English translation of Notification of the First Office Action", CN Application No. 202210206727.X dated Aug. 26, 2023, Beijing China (3 pages).
"English translation of Notification of the Second Office Action", CN Application No. 202210206727.X dated Dec. 6, 2022, Beijing China (3 pages).
"English translation of Notification of Decision of Granting Patent Right For Invention", CN Application No. 202210206727.X dated Mar. 29, 2029, Beijing China (2 pages).
English Translation of "Research on the Multifield Coupling Mechanism of Dynamic Water Grouting Diffusion in Fractured Rock Mass, " Ding Yang Zhang, Engineering Science and Technology of the Full Text Database of Chinese Doctoral Dissertations, Part 1, p. 119-121, Dec. 2018 (7 pages).

* cited by examiner

GROUTING AND WATER-PLUGGING DEVICE FOR FRACTURED ROCK IN MINE COUPLING STATE, AND TEST METHOD

FIELD

The present disclosure relates to the technical field of rock mechanics testing, and in particular, to a grouting and water-plugging device for a fractured rock in a mine coupling state, and a test method.

BACKGROUND

As the mining depth increases, a large number of wing-shaped micro cracks are more likely to form, affected by mining activities, inside a deep rock especially under the "three-high" (high stress, high earth temperature, and high water pressure) condition. These micro cracks are interconnected under the combined propagation effect of floor strata stress and water pressure infiltration, which increases the permeability of the rock and the probability of water gushing disasters, and brings serious hidden dangers to safe production of coal mines. Therefore, how to effectively plug the cracks generated in the rock is the key to controlling such disasters. The grouting and water-plugging technology for rock cracks is one of the effective measures to prevent and control mine water disasters and ensure safe mining.

The existing test equipment mostly focuses on a single factor in the study of crack propagation in a rock. The influence of a single factor on the rock cannot fully reflect the actual changes in the rock and the water gushing conditions. Therefore, it is necessary to consider the changes in crack propagation in the rock under coupling factors and verify the crack plugging effect after the rock is fractured. The inventor of the present disclosure conducted rock crack propagation testing under coupling conditions and verified the effectiveness of crack plugging, and provided a reliable basis for safe mining of coal mines.

SUMMARY

In order to conduct rock crack propagation testing under a coupling effect of deep-mine stress-temperature-water pressure, and reveal the crack propagation pattern of the rock under different conditions of water pressure, temperature, and stress, the inventor of the present disclosure conducted grouting and water-plugging tests on rock cracks, verified the effectiveness of crack plugging, and provided a reliable basis for safe mining of coal mines. The present disclosure provides a grouting and water-plugging device for a fractured rock in a mine coupling state and a test method. The specific technical scheme is as follows.

A grouting and water-plugging device for a fractured rock in a mine coupling state, includes a pressurizer, a reservoir, a test box, and a grouting pump. The reservoir includes a temperature sensor and a pressing-water plate. The pressing-water plate is connected to the pressurizer through a pressurizing rod. A pressure measuring pipe and a drainage pipe are installed on a side wall of the reservoir. The reservoir is connected to a water pump through a water injection pipe. The test box includes a transverse force exerting plate, a longitudinal force exerting plate, a stress sensor and the temperature sensor. A base is connected to a bottom plate and the transverse force exerting plate through an electric push rod. The transverse force exerting plate is connected to the longitudinal force exerting plate through the electric push rod. The longitudinal force exerting plate is provided with multiple water through holes. A sliding box door is hinged to a front wall of the test box. The pressure measuring pipe and the drainage pipe are installed on a rear wall of the test box. The rear wall of the test box is connected to the grouting pump through a grouting pipe.

Preferably, the pressurizer is configured to push the pressing-water plate to apply axial pressure to water flow, and left and right struts are configured to push the transverse force exerting plate to apply transverse pressure to a rock specimen.

Preferably, pressure measuring pipes are uniformly arranged on symmetrical side walls of the reservoir, and the temperature sensor is arranged in the reservoir.

Preferably, water pressure gauges are installed on the grouting pipe and the pressure measuring pipe, and valves are installed on the grouting pipe, the pressure measuring pipe, the water injection pipe, and the drainage pipe respectively.

Preferably, the transverse force exerting plates are symmetrical and respectively arranged on the left and right struts in the test box, and the longitudinal force exerting plate is provided with multiple water through holes.

Preferably, the sliding box door is provided with a handle, and one side of the sliding box door is magnetically connected to the test box; the sliding box door is covered with a thermal insulation layer, and outer layers of the reservoir and the test box are both covered with the thermal insulation layer.

Preferably, a control panel is installed adjacent to the test box, and a single-chip microcomputer is installed inside the control panel. The control panel is further provided with a liquid crystal display screen and control buttons. The single-chip microcomputer is connected to the sensors, the liquid crystal display screen, the control buttons, and the electric push rod.

A test method for grouting and water-plugging a fractured rock in a mine coupling state, utilizes the grouting and water-plugging device for a fractured rock in a mine coupling state according to any one of the above aspects, and includes the following steps:

A, preparing a rock specimen and placing it in the test box, and conducting a coupling test of stress-temperature-water pressure to determine a propagation pattern of rock fractures;

B. closing the water through holes, opening the valve on the grouting pipe, and injecting, by the grouting pump, a water plugging material into the test box to grout the rock specimen after the coupling test of stress-temperature-water pressure; and C. cleaning the test box, and conducting the coupling test of stress-temperature-water pressure again on the rock specimen after grouting to determine the effectiveness of grouting and water plugging.

Preferably, water is injected into the reservoir by the water pump. The pressurizer pushes the pressing-water plate to force the water flow to pass through the water through holes on the longitudinal force exerting plate and apply axial pressure to the rock specimen, where the pressure value of the water pressure gauge on the pressure measuring pipe is recorded; and the pressurizer pushes the transverse force exerting plate via the left and right struts to apply transverse pressure to the rock, where the pressure value is recorded.

Preferably, the valve on the grouting pipe is opened, and the cracks in the fractured rock specimen are plugged via the grouting pipe, where the grouting pressure is recorded. Step C is repeated to determine the effectiveness of water plugging.

The grouting and water-plugging device for a fractured rock in a mine coupling state and the test method according to the present disclosure have the following beneficial effects: environmental conditions can be flexibly changed for the rock specimen, the crack propagation pattern and the water gushing condition of the rock under coupling conditions of stress-temperature-water pressure can be stimulated, and the effectiveness of grouting and water plugging can be verified; the test device is provided with the thermal insulation layer, so that the accuracy of test results is improved; and, the test device also provides precise and controllable ways to apply axial pressure and transverse pressure, thereby providing a reliable basis for safe mining conditions in coal mines.

Figure 1:
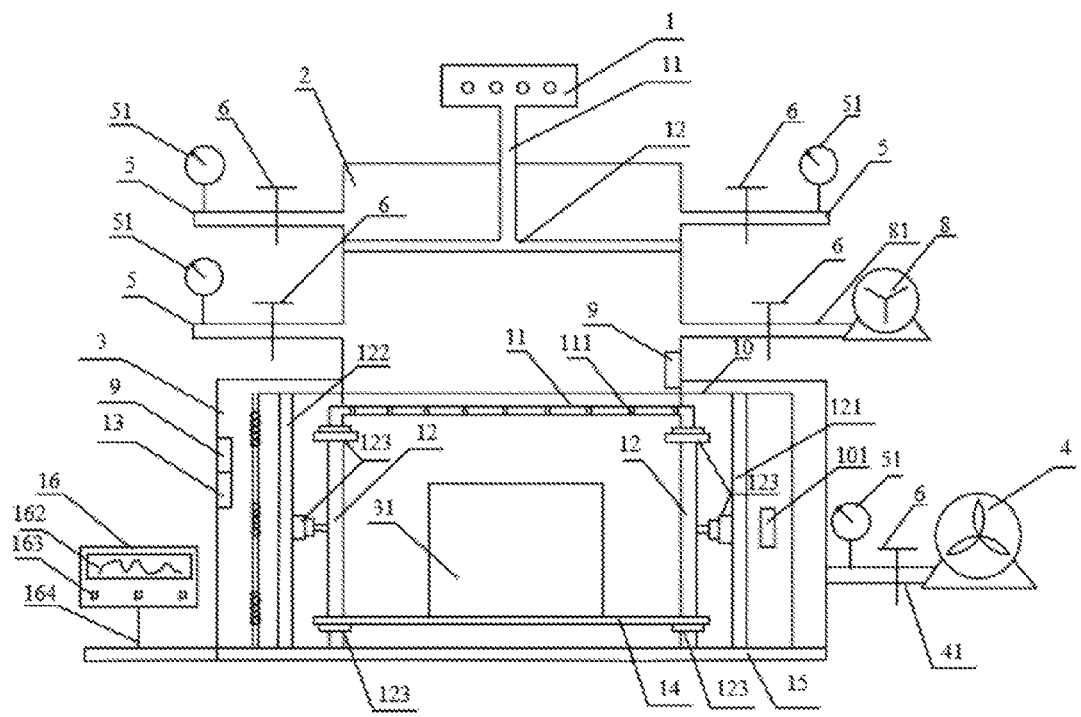
FIG. 1 is a schematic structural diagram of a grouting and water-plugging device for a fractured rock in a mine coupling state.

In the drawings: 1 pressurizer, 11 pressurizing rod, 12 pressing-water plate, 2 reservoir, 3 test box, 31 rock specimen, 4 grouting pump, 41 grouting pipe, 5 pressure measuring pipe, 51 water pressure gauge, 6 valve, 7 drainage pipe, 71 flow meter, 8 water pump, 81 water injection pipe, 9 temperature sensor, 10 sliding box door, 101 door handle, 11 longitudinal force exerting plate, 111 water through hole, 12 transverse force exerting plate, 121 right strut, 122 left strut, 123 electric push rod, 13 stress sensor, 14 base, 15 bottom plate, 16 control panel, 161 liquid crystal display screen, 162 control button, 163 pillar.

DETAILED DESCRIPTION OF THE EMBODIMENTS

Figure 2:
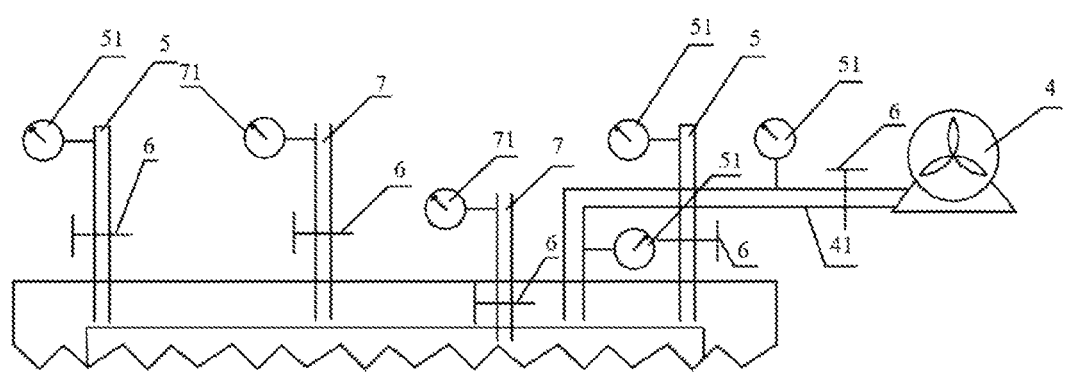
FIG. 2 is a top view of the pipeline connection between a test box and a reservoir.

Specific embodiments of a grouting and water-plugging device for a fractured rock in a mine coupling state and a test method according to the present disclosure are described below with reference to FIG. 1 and FIG. 2.

The grouting and water-plugging device for a fractured rock in a mine coupling state, includes a pressurizer 1, a reservoir 2, a test box 3, and a grouting pump 4. The pressurizer is used to apply axial force to water flow to simulate the water pressure of groundwater, the reservoir is used to provide and stimulate a water source through connections such as water pipes, the overall structure of the test box cooperates with the test specimen to complete the simulation test in the test box, and the grouting pump simulates the practical grouting situation through pipelines, so as to conduct a test under coupling conditions of stress-temperature-water pressure.

The reservoir 2 includes a temperature sensor 9 and a pressing-water plate 12. The pressing-water plate 12 is connected to the pressurizer 1 through a pressurizing rod 11. A pressure measuring pipe 5 and a drainage pipe 7 are installed on a side wall of the reservoir 2. The reservoir 2 is connected to a water pump 8 through a water injection pipe 81. The test box includes a transverse force exerting plate 12, a longitudinal force exerting plate 11, a stress sensor 13 and the temperature sensor 9. A base 14 is connected to a bottom plate 14 and the transverse force exerting plate through an electric push rod 123. The transverse force exerting plate 12 is connected to the longitudinal force exerting plate 11 through the electric push rod 123. The longitudinal force exerting plate 11 is provided with multiple water through holes 111. A sliding box door is hinged to a front wall of the test box 3. The pressure measuring pipe and the drainage pipe 7 are installed on a rear wall of the test box 3. The rear wall of the test box 3 is connected to the grouting pump 4 through a grouting pipe.

The pressurizer 1 is configured to push the pressing-water plate 12 to apply axial pressure to the water flow, to simulate the water pressure of groundwater. A left strut 122 and a right strut 121 are configured to push the transverse force exerting plate to apply transverse pressure to a rock specimen. The transverse force exerting plates 12 are symmetrical and respectively arranged on the left strut 122 and the right strut 121 in the test box, and the longitudinal force exerting plate is provided with multiple water through holes 111. The water through holes 111 allow the water flow in the reservoir 2 to be pressed into the test box 3. The size of the water through holes 111 can be changed to simulate the underground water flow of different flow rates.

Pressure measuring pipes 5 are uniformly arranged on symmetrical side walls of the reservoir 2, and the temperature sensor 9 is installed in the reservoir. A water pressure gauge is installed on the grouting pipe 41. A water pressure gauge 51 is installed on the pressure measuring pipe, so as to measure the water pressure value of the water flow at the pressure measuring pipe 5. The water pressure gauge 51 can use a common U-type manometer. Valves are installed on the grouting pipe 41, the pressure measuring pipe 5, the water injection pipe 81, and the drainage pipe 7 respectively. The grouting pipe 41 and the grouting pump 4 are used to inject a water plugging material into the test box 3. The water pressure gauge 51 is installed on the grouting pipe 41, so as to read the pressure value of grouting.

The drainage pipe 7 is installed on the rear wall of the reservoir 2, and a flow meter 71 is installed on the drainage pipe 7 to display the water flow rate. The right wall of the reservoir 2 is connected to the water pump 8 through the water injection pipe 81. The water pump 8 is used to inject water into the reservoir 2. The temperature sensor 9 is installed in the reservoir 2 to measure the water temperature in the reservoir 2.

A handle 101 is provided on a sliding box door 10. One side of the sliding box door 10 is magnetically connected to the test box. The sliding box door 10 is covered with a thermal insulation layer, and outer layers of the reservoir 2 and the test box 3 are both covered with the thermal insulation layer.

A control panel 16 is installed adjacent to the test box 3, and a single-chip microcomputer is installed inside the control panel. The control panel 16 is further provided with a liquid crystal display screen and control buttons. The single-chip microcomputer is connected to the sensors, the liquid crystal display screen, the control buttons, and the electric push rod. During the test, the temperature sensor 9 and the stress sensor 13 transmit data to the single-chip microcomputer 161; the single-chip microcomputer 161 transmits data to the liquid crystal display screen 162; and the liquid crystal display screen 162 converts the received data into a string diagram, which is more convenient for data comparison, analysis, and recording.

The test box 3 is fixedly installed on a bottom plate 15. A rock specimen 31, the temperature sensor 9, the longitudinal force exerting plate 11, the transverse force exerting plate 12, and the stress sensor 13 are provided inside the test box 3. The base 14 is connected to the bottom plate 15 and the transverse force exerting plate 12 through the electric push rod 123. The transverse force exerting plate 12 is connected to the longitudinal force exerting plate 11 through the electric push rods 123 respectively installed on the right strut 121 and the left strut 122. The longitudinal force exerting plate 11 and the transverse force exerting plate 12 respectively apply axial and transverse stresses to the rock specimen 31 to simulate the stresses borne by a rock in a mine. The temperature sensor 9 is used to measure the temperature of the environment where the rock specimen 31 is located, and the stress sensor 13 is used to measure the value of stress borne by the rock specimen 31.

A test method for grouting and water-plugging a fractured rock in a mine coupling state, utilizes the grouting and water-plugging device for a fractured rock in a mine coupling state according to any one of the above aspects, and includes the following steps:
  A. preparing a rock specimen and placing it in the test box, and conducting a coupling test of stress-temperature-water pressure to determine a propagation pattern of rock fractures; where the rock specimen is loaded with a coupling load, and test data such as pressure values are recorded to analyze the development of propagation of rock fractures.
  B. closing the water through holes, opening the valve on the grouting pipe, injecting, by the grouting pump, a water plugging material into the test box to grout the rock specimen after the coupling test of stress-temperature-water pressure, and recording a grouting pressure.
  C. cleaning the test box, and conducting the coupling test of stress-temperature-water pressure again on the rock specimen after grouting to determine the effectiveness of grouting and water plugging.

During the test, water is injected into the reservoir by the water pump. The pressurizer pushes the pressing-water plate to force the water flow to pass through the water through holes on the longitudinal force exerting plate and apply axial pressure to the rock specimen, where the pressure value of the water pressure gauge on the pressure measuring pipe is recorded; and the pressurizer pushes the transverse force exerting plate via the left and right struts to apply transverse pressure to the rock, where the pressure value is recorded. The valve on the grouting pipe is opened, and the cracks in the fractured rock specimen are plugged via the grouting pipe, where the grouting pressure is recorded. Step C is repeated to determine the effectiveness of water plugging.

A test of a single factor or multiple factors can be conducted on different types of rocks in the test box 3 of the grouting and water-plugging device for a fractured rock in a mine coupling state.

By selecting different types of rock specimens 31 and changing the environment in which the rock specimens 31 are located, the crack propagation pattern and the water gushing condition of the rock 31 under coupling conditions of stress-temperature-water pressure can be stimulated, and the effectiveness of grouting and water plugging can be verified. By wrapping the thermal insulation layer around the reservoir 2, the test box 3, and the sliding box door 10, the accuracy of the test results can be improved. In addition, the test device can further improve the accuracy of the test results by providing the thermal insulation layer. The test device also provides precise and controllable ways to apply axial pressure and transverse pressure, ensuring the operability of the test and thereby providing a reliable basis for safe mining conditions in coal mines.

The above description is not intended to limit the present disclosure, and the present disclosure is not limited to the above examples either. Any changes, modifications, additions or replacements made, by those skilled in the art, within the substantive scope of the present disclosure should also fall within the scope of protection of the present disclosure.

The invention claimed is:
1. A test method for grouting and water-plugging a fractured rock in a mine coupling state, utilizing a grouting and water-plugging device for a fractured rock in a mine coupling state, characterized by comprising a pressurizer, a reservoir, a test box, and a grouting pump, wherein the reservoir comprises a temperature sensor and a pressing-water plate, the pressing-water plate is connected to the pressurizer through a pressurizing rod, a pressure measuring pipe and a drainage pipe are installed on a side wall of the reservoir, and the reservoir is connected to a water pump through a water injection pipe; the test box comprises a transverse force exerting plate, a longitudinal force exerting plate, a stress sensor and the temperature sensor, a base is connected to a bottom plate and the transverse force exerting plate through an electric push rod, the transverse force exerting plate is connected to the longitudinal force exerting plate through the electric push rod, the longitudinal force exerting plate is provided with a plurality of water through holes, a sliding box door is hinged to a front wall of the test box, the pressure measuring pipe and the drainage pipe are installed on a rear wall of the test box, and the rear wall of the test box is connected to the grouting pump through a grouting pipe; the pressurizer is configured to push the pressing-water plate to apply axial pressure to water flow, and a left strut and a right strut are configured to push the transverse force exerting plate to apply transverse pressure to a rock specimen; pressure measuring pipes are uniformly arranged on symmetrical side walls of the reservoir, and the temperature sensor is arranged in the reservoir; water pressure gauges are installed on the grouting pipe and the pressure measuring pipe, and valves are installed on the grouting pipe, the pressure measuring pipe, the water injection pipe, and the drainage pipe respectively; the transverse force exerting plates are symmetrical and respectively arranged on a left strut and a right strut in the test box; the sliding box door is provided with a handle, and one side of the sliding box door is magnetically connected to the test box; the sliding box door is covered with a thermal insulation layer, and outer layers of the reservoir and the test box are both covered with the thermal insulation layer; a control panel is installed adjacent to the test box, and a single-chip microcomputer is installed inside the control panel, wherein the control panel is further provided with a liquid crystal display screen and control buttons, and the single-chip microcomputer is connected to the sensors, the liquid crystal display screen, the control buttons, and the electric push rod; the test method comprising:
  A. preparing a rock specimen and placing it in the test box, and conducting a coupling test of stress-temperature-water pressure to determine a propagation pattern of rock fractures;
  B. closing the water through holes, opening the valve on the grouting pipe, and injecting, by the grouting pump, a water plugging material into the test box to grout the rock specimen after the coupling test of stress-temperature-water pressure; and
  C. cleaning the test box, and conducting the coupling test of stress-temperature-water pressure again on the rock specimen after grouting to determine the effectiveness of grouting and water plugging;
  wherein water is injected into the reservoir by the water pump, and the pressurizer pushes the pressing-water plate to force the water flow to pass through the plurality of water through holes on the longitudinal force exerting plate and apply axial pressure to the rock specimen, wherein a pressure value of the water pressure gauge on the pressure measuring pipe is recorded; and the pressurizer pushes the transverse force exerting plate via the left strut and the right strut to apply transverse pressure to the rock, wherein the pressure value is recorded, wherein the valve on the grouting pipe is opened, and cracks in the fractured rock specimen are plugged via the grouting pipe, wherein a grouting pressure is recorded, and wherein step C is repeated to determine the effectiveness of water plugging.

* * * * *